(12) United States Patent
Burkhardt et al.

(10) Patent No.: US 6,717,005 B2
(45) Date of Patent: Apr. 6, 2004

(54) EPOXY-STABILIZED POLYPHOSPHATE COMPOSITIONS

(75) Inventors: Eric W. Burkhardt, Brewster, NY (US); Danielle A. Bright, New City, NY (US); Sergei Levchik, Croton-on-Hudson, NY (US); Sophia Dashevsky, Fairlawn, NJ (US); Mark Buczek, Sleepy Hollow, NY (US)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/144,568

(22) Filed: May 13, 2002

(65) Prior Publication Data

US 2003/0212287 A1 Nov. 13, 2003

(51) Int. Cl.$^7$ .................................................. C07F 9/02
(52) U.S. Cl. ........................................ 558/146; 558/147
(58) Field of Search .................................. 558/146, 147

(56) References Cited

U.S. PATENT DOCUMENTS

| | | | |
|---|---|---|---|
| 3,637,507 A | 1/1972 | Gentit | 252/78 |
| 3,932,294 A | 1/1976 | Burrous | 252/78 |
| 3,941,708 A | 3/1976 | Gentit et al. | 252/78 |
| 4,696,963 A | 9/1987 | Albright et al. | 524/144 |
| 4,992,496 A | 2/1991 | Green | 524/109 |
| 5,464,551 A | 11/1995 | Deetman | 252/78.5 |
| 5,616,768 A | 4/1997 | Kawata et al. | 558/146 |
| 5,871,570 A | 2/1999 | Koyama et al. | 106/18.18 |

FOREIGN PATENT DOCUMENTS

| | | | |
|---|---|---|---|
| EP | 909790 | 4/1999 | ........... C08L/69/00 |
| JP | 2001-002945 | 1/2001 | ......... C08L/101/16 |
| JP | 2001/-131392 | 5/2001 | ........... C08L/63/00 |
| JP | 2001-151786 | 6/2001 | ............. C07F/9/09 |
| WO | 01/85881 | 11/2001 | ........ C10M/169/04 |

OTHER PUBLICATIONS

CA Plus Abstract of Japanese Patent No. 2001–151786.
Derwent Abstract 2001–218340/22 (2001).
Derwent Abstract 2001–260398/27 (2001).

*Primary Examiner*—Joseph K. McKane
*Assistant Examiner*—Kamal Saeed
(74) *Attorney, Agent, or Firm*—Richard P. Fennelly

(57) ABSTRACT

A polyphosphate ester composition consisting essentially of an effective amount of a cycloaliphatic epoxy composition for reduction of the total acid number of the composition. The phosphate ester is of the formula:

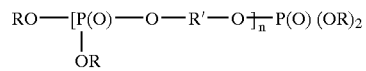

where R can be aryl or alkaryl, R' can be arylene, arylene-alkylene-arylene, or alkylene, and n ranges from about 1 to about 5.

8 Claims, No Drawings

EPOXY-STABILIZED POLYPHOSPHATE COMPOSITIONS

BACKGROUND OF THE INVENTION

It is known to add epoxy compounds as stabilizers to monophosphate compounds that find utility as functional fluids. Examples of patents describing such an approach include: U.S. Pat. Nos. 3,637,507 to W. F. Gentit; 3,932,294 to M. L. Burrous; and 3,941,708 to W. F. Gentit et al.

A class of distinctly differing polyphosphate compound is also known that has the formula:

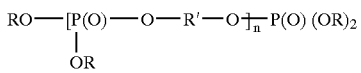

where n, on a number average basis, ranges from about 1 to about 5 R is aryl, such as phenyl, or alkaryl, and R' is arylene (such as derived from resorcinol), arylene-alkylene-arylene (such as derived from bisphenol A), or alkylene (such as neopentylene). These polyphosphate esters are used, for example, as flame retardants and plasticizers for plastics and are prone to hydrolysis that produce phosphoric acids that are undesirable degradation products. These acid species can cause decomposition of polycarbonate resins.

Various approaches are described to solve the aforementioned problems of degradation. European Patent No. 909,790 to General Electric Company describes the addition of an acid scavenger, such as an epoxy compound, to a composition comprising the polyphosphate and the resin. In U.S. Pat. No. 5,871,570 to T. Koyama a similar approach is advocated where an epoxy compound not containing halogen is added to a polycarbonate resin composition containing an organic phosphorus-type flame retardant and other additives. Japanese Published Patent Application No. 2001/2945 describes adding an alicyclic epoxy compound to a resin composition that also contains an organic phosphorus flame retardant. In this general approach the epoxy compound is added to the polyphosphate only after it has been to the resin system that it is intended to also contain the flame retardant.

Another approach has been to add the epoxy compound to the polyphosphate at some point in its manufacturing process after it has been formed. PCT Published Patent Application No. 2001/12638 to Daihachi describes treating the phosphate compound with epoxy and then with an aqueous alkali solution. U.S. Pat. No. 5,616,768 to S. Kawata treats a crude phosphate product with an epoxy compound, heats the resulting product in the presence of water, washes the product with water, and removes the residual water. Japanese Published Patent Application No. 2001/151,786 describes an aromatic polyphosphate composition that is stabilized by the addition of bis(2,4-di-tert-butylphenyl) pentaerythritol diphosphite and 3,4-epoxycyclohexylmethyl 3,4-epoxycyclohexanecarboxylate.

Japanese Patent Publication No. 2001/131,392 (May 15, 2001) illustrates a flame retardant composition that comprises an organophosphorus compound and an epoxy compound having an acid number of 1 or less.

DESCRIPTION OF THE INVENTION

This invention relates to such polyphosphate compositions that have been stabilized by the addition of a certain class of epoxy stabilizer. This invention allows for a polyphosphate/epoxy stabilizer pre-mix that can thereafter be added to a substrate resin (e.g., an engineering resin) to stabilize the final flame retarded resin formulation.

The epoxy stabilizer of choice herein is one or more cycloaliphatic epoxy compounds having a $C_6$ to $C_{20}$ cycloaliphatic ring. They are alicyclic epoxy compounds where the alicyclic epoxy structural units are linked through a bonding unit, which is either a dioxane, or a carboxyl structural unit. Useful cycloaliphatic epoxy compounds include: 3,4 epoxycyclohexylmethyl 3,4 epoxycyclohexane carboxylate, which is available as ERL-4221 (a Union Carbide Corporation trademark) and ARALDITE CY-179 (a Ciba-Geigy trademark); the diglycidyl ester of hexahydrophthalic anhydride, which is available as CY-184 (a Ciba-Geigy trademark); bis(3,4-epoxycyclohexylmethyl)adipate, which is available as ERL-4299 (a Union Carbide trademark), vinyl cyclohexene dioxide (ERL-4206), vinyl cyclohexene monoxide, and 2-[3,4-epoxycyclohexyl-5,5-spiro-3,4-epoxy]-cyclohexane-meta-dioxane (ERL-4234]. In general, this epoxy component can be selected from the cycloaliphatic epoxides (including diepoxides). Examples of such structures are shown below:

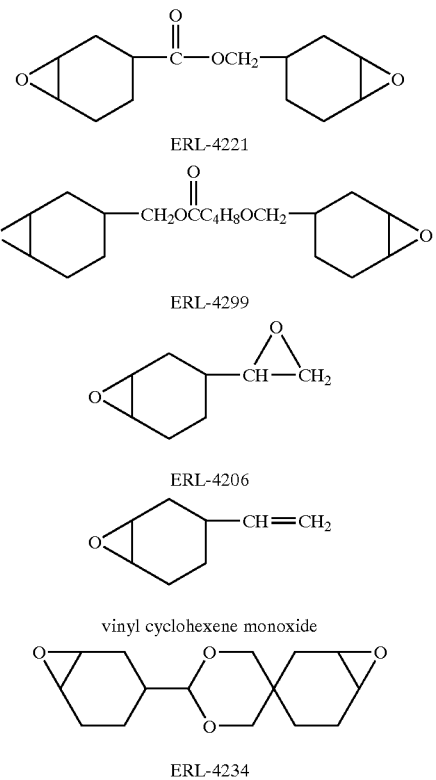

The addition of 3,4-epoxycyclohexylmethyl 3,4-epoxycyclohexane carboxylate (ERL 4221 from Union Carbide) to these polyphosphate esters is preferred and prevents the formation of acidic species under conditions of high temperature and humidity and gives polyphosphate esters of high hydrolytic stability which can then be added, if desired, to resins to stabilize the resulting resin.

In general terms, the amount of epoxy to use will range from about 0.01% to about 1%, by weight of the polyphosphate composition. The admixture of polyphosphate and epoxy additive are advantageously allowed to stand at a temperature of from above about room temperature to 150° C. for periods of time ranging from about eight hours to about fifteen minutes, respectively.

The stabilized polyphosphate compositions of this invention, when treated with water at 90° C. for thirty-five days, for example, do not show an increase in acidity thus demonstrating their attractive hydrolytic stability characteristics. The present invention will be further understood by the Examples that follow.

EXAMPLE 1

Bisphenol A bis(diphenyl phosphate), 497.5 g, having an acid number of 0.059 mg. KOH/g and 2.5 g. of 3,4-epoxycyclohexylmethyl 3,4-epoxycyclohexane carboxylate (ERL-4221 brand from Union Carbide) were mixed at 40° C. and stirred for four hours. After that time, the acid number was measured and was found to be 0.044 mg of KOH/g.

EXAMPLE 2

A similar amount of 1 Bisphenol A bis(diphenyl phosphate), as used in Example 1, having an acid number of 0.059 mg KOH/g. and 2.5 g. of DER-732 brand epoxy resin (a polyglycol epoxy resin) from Dow Chemical were mixed at 40° C. and stirred for four hours. After that period of time, the acid number was measured and was found to be 0.047 mg of KOH/g.

Hydrolytic Stability Testing of Epoxy-Stabilized Polyphosphate

The hydrolytic stability of this material was compared to that of the untreated sample using the following test procedure:

A 1-liter resin flask is charged with 400 grams of the phosphate ester and 4 grams (1 weight %) of distilled water. The resin kettle is equipped with a mechanical stirrer (glass rod, TEFLON fluorocarbon blade) and rubber septa to ensure an air tight system. The flask is immersed in an oil bath maintained at 93° C. The mixture is stirred at a rate of 120–150 rpm.

The system was sampled periodically for total acid number (TAN) analysis. A solution of about 0.01 M sodium hydroxide was used to titrate to a pale green endpoint using naphtholbenzein indicator (ASTM method D 948). The data is summarized in the following Table:

| | Results | | |
|---|---|---|---|
| Time (days) | Untreated BDP (mg. KOH/g.) | Sample 1 (mg. KOH/g.) | Sample 2 (mg. KOH/g.) |
| 0 | 0.059 | 0.044 | 0.047 |
| 2 | 0.074 | 0.001 | 0.035 |
| 7 | 0.127 | 0.001 | 0.475 |
| 9 | 0.159 | 0.001 | 0.608 |
| 13 | 0.246 | 0.001 | 1.147 |
| 15 | 0.317 | 0.001 | 1.140 |
| 23 | 0.85 | 0.002 | — |
| 30 | 1.39 | 0.002 | — |
| 35 | 2.07 | 0.003 | — |

The foregoing Examples are set forth to merely provide certain preferred embodiments of the present invention and, for that reason, should not be construed in a limiting sense. The scope of protection sought is set forth in the claims that follow.

We claim:

1. A stabilized polyphosphate ester composition consisting essentially of a polyphosphate ester represented by the formula:

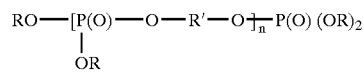

where R is selected from the group consisting of aryl and alkaryl, R' is selected from the group consisting of arylene, arylene-alkylene-arylene, and alkylene, and n ranges from about 1 to about 5 and an effective amount of a cycloaliphatic epoxy composition for reduction of the total acid number of the composition.

2. A composition according to claim 1 where R is phenyl and —O—R—O— is a bisphenol A moiety.

3. A composition according to claim 1 where R is phenyl and —O—R—O— is a resorcinol moiety.

4. A composition according to claim 1 where R is phenyl and —O—R—O— is a neopentyl glycol moiety.

5. A composition according to claim 1 where R is 2,6-xylenol.

6. A composition as claimed in any of claims 1 and 3 to 6 wherein the epoxy composition is 3,4-epoxycyclohexylmethyl 3,4-epoxycyclohexane carboxylate.

7. A composition as claimed in any of claims 1 and 3 to 6 wherein the epoxy composition is present at from about 0.01% to about 1%, by weight of the polyphosphate composition.

8. A composition as claimed in any of claims 1 and 3 to 6 wherein the polyphosphate and epoxy additive are allowed to stand together at a temperature of from above about room temperature to 150° C. for periods of time ranging from about eight hours to about fifteen minutes, respectively.

* * * * *

UNITED STATES PATENT AND TRADEMARK OFFICE
CERTIFICATE OF CORRECTION

PATENT NO.   : 6,717,005 B2
DATED        : April 6, 2004
INVENTOR(S)  : Eric W. Burkhardt et al.

It is certified that error appears in the above-identified patent and that said Letters Patent is hereby corrected as shown below:

<u>Column 4,</u>
Lines 40-51, "claims 1 and 3 to 6" should read -- claims 2 to 5 --.

Signed and Sealed this

Nineteenth Day of April, 2005

JON W. DUDAS
*Director of the United States Patent and Trademark Office*